US010980713B2

(12) United States Patent
Maier et al.

(10) Patent No.: US 10,980,713 B2
(45) Date of Patent: Apr. 20, 2021

(54) DENTAL COMPOSITION

(71) Applicant: DENTSPLY SIRONA Inc., York, PA (US)

(72) Inventors: Maximilian Maier, Düsseldorf (DE); Huaibing Liu, Dover, DE (US); Sven Pohle, Constance (DE); Florian Szillat, Constance (DE)

(73) Assignee: DENTSPLY SIRONA INC., York, PA (US)

( * ) Notice: Subject to any disclaimer, the term of this patent is extended or adjusted under 35 U.S.C. 154(b) by 131 days.

(21) Appl. No.: 16/296,307

(22) Filed: Mar. 8, 2019

(65) Prior Publication Data

US 2019/0274930 A1    Sep. 12, 2019

Related U.S. Application Data

(60) Provisional application No. 62/640,052, filed on Mar. 8, 2018.

(30) Foreign Application Priority Data

Mar. 21, 2018    (EP) .................................... 18163137

(51) Int. Cl.
| | |
|---|---|
| *A61K 6/889* | (2020.01) |
| *A61K 6/887* | (2020.01) |
| *A61K 6/891* | (2020.01) |
| *A61K 6/17* | (2020.01) |
| *A61K 6/71* | (2020.01) |
| *A61K 6/824* | (2020.01) |

(52) U.S. Cl.
CPC ................ *A61K 6/891* (2020.01); *A61K 6/17* (2020.01); *A61K 6/71* (2020.01); *A61K 6/824* (2020.01); *A61K 6/887* (2020.01); *A61K 6/889* (2020.01)

(58) Field of Classification Search
CPC ....................................................... A61K 6/889
See application file for complete search history.

(56) References Cited

U.S. PATENT DOCUMENTS

| | | | | |
|---|---|---|---|---|
| 5,814,682 | A * | 9/1998 | Rusin ........................ | A61K 6/77 523/116 |
| 7,541,393 | B2 * | 6/2009 | Mitra ..................... | C07C 335/10 523/116 |
| 8,198,388 | B2 * | 6/2012 | Klee ......................... | A61K 6/30 526/277 |
| 2014/0039087 | A1 * | 2/2014 | Stelzig ................... | A61K 6/889 523/113 |
| 2014/0228474 | A1 * | 8/2014 | Qian ...................... | A61K 6/887 523/116 |
| 2015/0314554 | A1 * | 11/2015 | Fujiwara ............... | B32B 27/302 428/35.7 |

FOREIGN PATENT DOCUMENTS

| | | |
|---|---|---|
| EP | 1548021 A1 | 6/2005 |
| EP | 1601679 A2 | 12/2005 |
| EP | 2236122 A2 | 10/2010 |
| EP | 2764859 A2 | 8/2014 |

OTHER PUBLICATIONS

PCT International Search Report, application No. PCT/US2019/021248.
PCT International Written Opinion, application No. PCT/US2019/021248.
European Search Report, dated Oct. 16, 2018.
J. E. Klee et al, "Novel 2-(omega-phosphonooxy-2-oxaalkyl)acrylate monomers for self-etching self-proming one part adhesive", Beilstein Journal of Organic Chemistry, 2010, p. 766-772,vol. 6, Germany.

* cited by examiner

*Primary Examiner* — Michael F Pepitone
(74) *Attorney, Agent, or Firm* — Dentsply Sirona Inc.

(57) ABSTRACT

Disclosed is a resin modified dental luting cement composition having a polymerizable resin component, a polyacidic polymer component, a filler component, a redox initiator system, and water.

12 Claims, 9 Drawing Sheets

DENTAL COMPOSITION

FIELD OF THE INVENTION

The present invention relates to a resin modified dental luting cement composition, notably a resin modified dental implant cement composition. Moreover, the present invention relates to the use of the resin modified dental luting cement composition according to the present invention for luting implant-retained restorations such as crowns and dentures, notably for adhering an implant-retained restoration to an abutment. Finally, the present invention relates to a use of a specific compound for preparing a dental cement composition.

The resin modified dental luting cement composition provides at the same time excellent crown retention and crown removability.

BACKGROUND OF THE INVENTION

A luting cement is a curable paste used to attach indirect restorations to prepared teeth or abutments as shown in FIG. 15. Depending on the expected longevity of the restoration, a luting cement can be considered to be definitive (permanent) or provisional (temporary). Other classification may be based on main ingredients (e.g. zinc phosphate, zinc oxide-eugenol, zinc polycarboxylate, glass-ionomer, resin, resin modified glass ionomer), knowledge and experience of use (conventional vs. contemporary luting cements) or the principal setting-reaction (acid-base reaction vs. polymerization).

The primary function of a luting cement is to fill the void at the restoration-tooth/-abutment interface and mechanically and/or chemically lock the restoration in place in order to prevent its dislodgement during mastication. In particular, dental luting cement compositions are used for bonding a dental prosthesis such as a crown or partial denture to an abutment.

Cements, dedicated to connecting restorations to abutments are referred to as "implant cements" and compete with alternative ways of attachment, i.e. screw-retention and conventional cements dedicated to adhering to tooth structure.

A need to retrieve a cemented luting restorations can arise due to several factors, including a loose or broken screw, poor fitting margins, subgingival cement, irresolvable peri-implantitis, poor occlusion, or unsatisfactory esthetics.

In particular, during the lifetime of implant-carried restorations, the retaining screw between implant and abutment might loosen or even break. Accordingly, accessing and re-tightening or replacement of the screw might become necessary. Depending on the cement used, this can be tedious and may result in the destruction of the restoration. A dedicated implant cement should, therefore, be "strong" enough to keep a restoration in place, but "weak" enough to allow its removal.

Furthermore, the need for retrieval of a cemented luting restoration is even more urgent in view of the recognition of unique biological features of the peri-implant environment as well as in view of peri-implantitis.

Peri-Implantitis describes a syndrome of significant, progressive bone-loss around implants which occurs only 5-10 years after implant placement. If left untreated, enough bone is degenerated and implant failure/re-treatment is inevitable.

Due to the severity of the disease, its costs of re-treatment and average prevalence of more than 20% on a patient level, peri-implantitis is a focal point of implant dentistry.

Among the known risk-factors of the disease, residues of luting cements within the peri-implant tissues are commonly accepted and seen as an iatrogenic factor. Although their overall impact on the development of peri-implantitis is considered to be lower than e.g. the number of implants being placed per jaw or the overall status of periodontal health of a patient, dentists are sensitive towards this topic, sometimes avoiding cements altogether.

Cement residues may occur due to over-extrusion and/or insufficient clean-up after attachment of restorations. They may lead to physical irritation, foreign-body reaction and/or an accumulation of adverse strains of bacteria. The resulting inflammation affects soft-tissue (Mucositis) and then, if left untreated, hard-tissue (peri-implantitis). This chain of events is facilitated by a weaker seal of pen-implant tissue compared to the Periodontium, making it more prone to intrusion of external matter (e.g. excess cement). In many cases, the matter is difficult to detect and remove, particularly if the implant-abutment interface is placed sub-gingivally.

Depending on the reason for removal, in some instances the problem can be resolved and the prosthesis reused as a screw-retained definitive or provisional prosthesis. In such cases it is desirable to maintain integrity of the porcelain.

Removal of a cemented crown or fixed partial denture is a cumbersome procedure for a prosthodontist. Crown removal instruments with jerky removal force may damage the gingival/periodontal tissues or underlying tooth structure. In these situations, sectioning the crown rather than attempting to remove it intact is often required.

Accordingly, a dental luting cement composition should be adapted to allow removal of the cemented prosthesis by applying a force while at the same time securely attaching the artificial tooth to the abutment during normal use.

Temporary dental luting cement composition comprising self-curing zinc-oxide eugenol-based temporary cements are known from the prior art. For example, Temp-Bond™ (Kerr Corp.) is indicated for temporary crowns, bridges or splints, and for trial cementing permanent restorations. Although crown removability is excellent, the mechanical properties of the cured cement are inferior so that a use as a permanent cement is excluded, cf FIG. 9.

Non-eugenol semi-permanent cements for luting implant-retained restorations are also known. For example, Premier® Implant Cement (Premier® Dental Products Company) is a non-eugenol temporary cement comprising a silica filled triethylene glycol dimethacrylate resin which is self-cured by a peroxide polymerization initiator. Although the mechanical properties including crown retention are acceptable, the removal of a crown is hardly possible without destruction of the crown once the composition is cured, cf FIG. 9.

Permanent dental luting cement composition are also known from the prior art, and may be resin modified glass ionomer (RMGI) compositions or self-adhesive resin cement (SARC) compositions. For example, RelyX Luting Plus® (3M ESPE) is a resin modified glass ionomer cement composition providing a high level of mechanical properties whereas the removal of the crown is achieved only with great difficulty without destruction of the crown. Specifically, more than 6 attempts are required in the crown removal test which means an inacceptable burden on the patient when removing a prosthesis. Moreover, Calibra® Universal (DENTSPLY Sirona) is a universal self-adhesive resin cement providing an extremely high level of mechanical properties. Although crown removability is slightly easier than in the case of a temporary cement Premier®

Implant Cement, destruction of the crown cannot be avoided during the treatment of a patient, cf FIG. 9.

EP2764859 discloses a dental resin modified glass-ionomer composition including an acidic polymer, an acidic polymerizable monomer selected from 4-(meth)acryloxyalkyltrimellitic anhydride, 4-(meth)acryloxyalkyltrimellitic acid, and a combination thereof, a non-acidic polymerizable monomer, a fluoroaluminosilicate glass filler, water; and at least one polymerization initiator system. The dental resin modified glass-ionomer composition provides significantly enhanced adhesive property toward tooth structure.

EP2236122 discloses a polymer modified glass ionomer cement containing at least one polymer of an alpha, beta-unsaturated carboxylic acid, a basic glass composition, a radical polymerizable monomer, water, at least a polymerization initiator; and optionally conventional additives.

SUMMARY OF THE INVENTION

It is a problem of the present invention to provide a dental luting cement composition which provides
- optimal flow characteristics for avoiding that the cement drips during the treatment of the patient;
- easy seating of the restoration, in particular below the abutment-restoration margin;
- easy clean-up of excess cement to allow for a reliable clean-up procedure;
- high radiopacity to allow for detectability of residual cement;
- compatibility with titanium to avoid corrosion of titanium abutments;
- ideal mechanical strength to allow for a long-term cementation indication;
- antibacterial properties to avoid bacterial colonization of the cement;
- high moisture tolerance when applied; and
- easy removal/retrievability to allow for easy removal of the restoration.

The problem of the invention was solved according to the claims. Accordingly, the present invention provides a resin modified dental luting cement composition comprising
- (a) a polymerizable resin component;
- (b) a polyacidic polymer component;
- (c) a filler component comprising
  - (c1) a particulate zinc oxide containing filler adapted to be reactive with the polyacidic polymer component in a cement reaction, and
  - (c2) an inert particulate filler which cannot react with the polyacidic polymer in a cement reaction;
- (d) a redox initiator system for initiating polymerization of the polymerizable resin component, which comprises an oxidizing agent and a reducing agent; and
- (e) water.

Moreover, the present invention provides a resin modified dental luting cement composition according to the invention for use in adhering an implant restoration to an abutment Moreover, the present invention provides a use of a compound of the following formula (I):

(I)

wherein
$R^1$ and $R^2$
  which may be the same or different, independently represent a hydrogen atom or a $C_{1-6}$ alkyl group or a $C_{1-6}$ fluoroalkyl group;
$R^3$ which may be the same or different when more than one $R^3$ is present, independently represent a hydrogen atom or a $C_{1-6}$ alkyl group or a $C_{1-6}$ fluoroalkyl group;
$R^4$ represents a hydrogen atom or a $C_{1-6}$ alkyl group or a $C_{1-6}$ fluoroalkyl group;
a is an integer of from 1 to 4;
b is 0 or an integer of from 1 to 9; and
c is 0 or an integer of from 1 to 9,
for preparing a dental cement composition.

The present invention provides a composition combining properties of a zinc oxide cement with the formulation-flexibility of a resin cement based on a combination of an RMGI and a zinc oxide polycarboxylate.

The present invention is based on the recognition that it is possible to provide a dental luting cement composition which is stronger than conventional temporary implant cements in keeping a restoration in place, but much weaker than conventional permanent implant cements to allow easy removal without damage to the restoration.

The present invention uses a specific dual curing mechanism wherein a radically polymerizable resin component and a glass ionomer component form separate networks based on covalent bond formation and an acid-base reaction, respectively. At the same time, the networks are filled with an inert particulate filler so that cohesion and adhesion of the dental luting cement is reduced. As a result, a surprising combination of resistance to static mechanical forces and instability to dynamic forces is obtained.

Components (a) and (d) serve as the basis for the formation of a covalent resin network (A). Component (b) and (c1) serve as the basis of an ionic glass ionomer network (B). Component (c2) serves as a filler (C) which may modulate the mechanical properties by replacing covalent resin network and glass ionomer network in the cured resin modified dental luting cement composition according to the present invention. Accordingly, the resin modified dental luting cement composition according to the present invention may be conceptualized as a combination of a covalent network (A), an ionic network (B), which networks (A) and (B) may be interpenetrating, and an inert filler (C).

DESCRIPTION OF THE FIGURES

FIG. 3 shows results CR for Ex-1 to -5 (stainless-steel mock-crowns to titanium abutment).

FIG. 4 shows results CRB for Ex-1 to -5 (stainless-steel mock-crowns to titanium abutment).

FIG. 5 shows results CR for Ex-1 to -5 (zirconia mock-crowns to titanium abutment).

FIG. 6: shows results CRB for Ex-1 to -5 (zirconia mock-crowns to titanium abutment).

FIG. 7 shows results FS for Ex-1 to -5.

FIG. 8 shows results CS for Ex-1 to -5.

FIG. 9 shows a comparison of crown retention and crown removability. The large difference between high crown retention and low crown removability according to the present invention is unique among generic compositions.

FIG. 10 shows a comparison of flexural strength (FS).

FIG. 11 shows a comparison of flexural modulus (FM).

FIG. 12 shows a comparison of compressive strength (CS).

FIG. 13 shows a comparison of radioopacity (RO).

FIG. 14 shows a comparison of curing indicators including working time (wt) and setting time (st).

DESCRIPTION OF THE PREFERRED EMBODIMENTS

Figure 1:
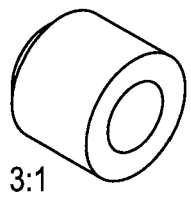
FIG. 1 shows a schematic view of mock-crowns, as fitted onto Ankylos Regular/X, AO abutments.
Figure 1:
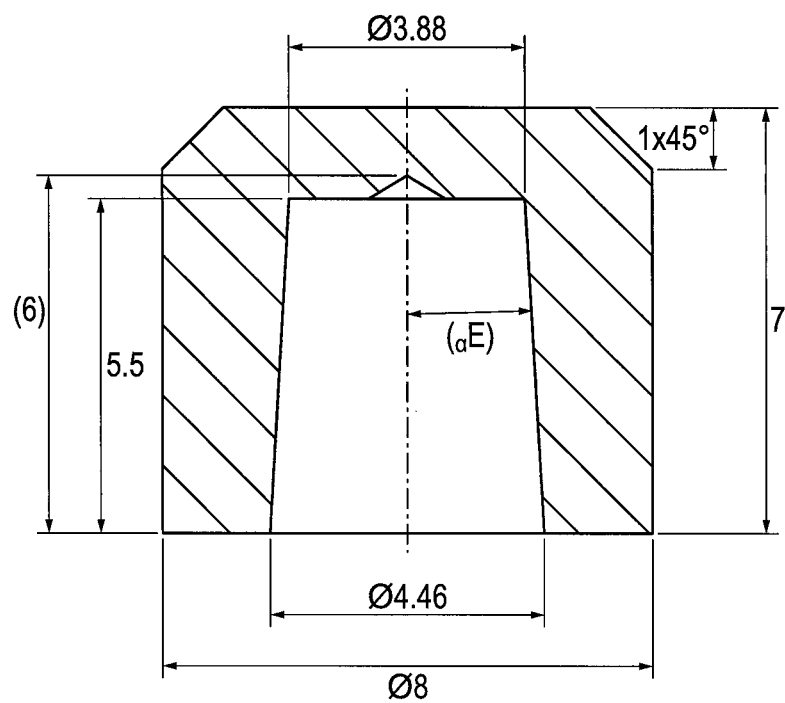
Figure 2:
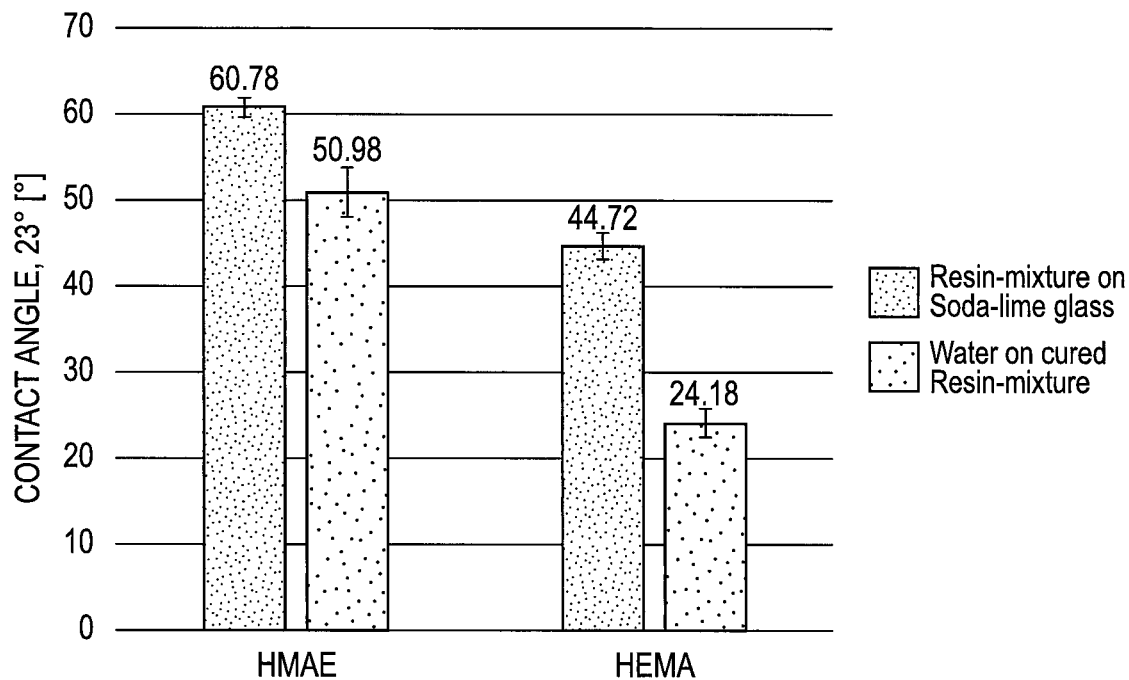
FIG. 2 shows the results of CA-measurements of HMAE- or HEMA-based resin-mixtures. Specifically, as can be seen, resin-mixtures, based on HMAE are more hydrophobic than resin-mixtures based on HEMA. Yet, they are hydrophilic enough to yield homogenous, smooth cement pastes according to table 4, #1-5 and 6c.
Figure 3:
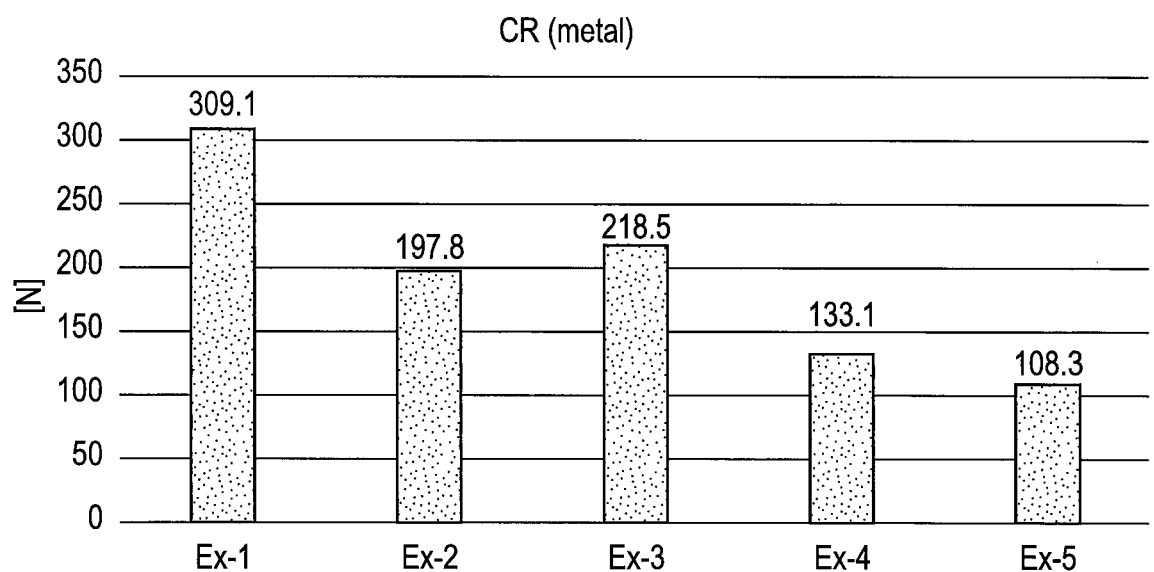
FIG. 3-6 show the evolution of retention force (to metal or zirconia) and the removability according to changes in the overall cement formulation (cf. tables 1, 2 and 4). Specifically.
Figure 4:
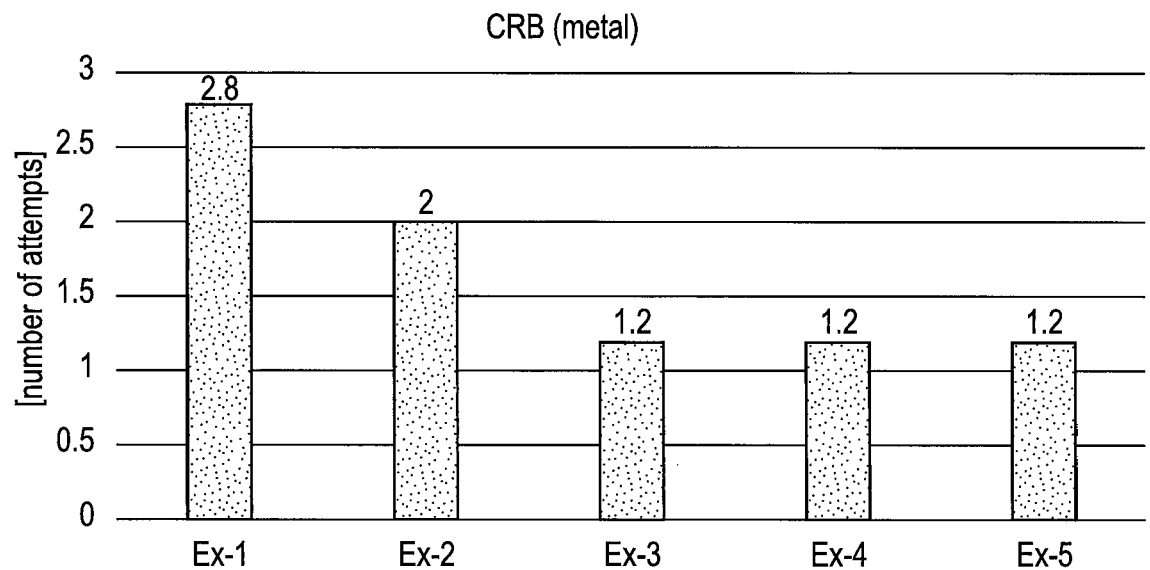
Figure 5:
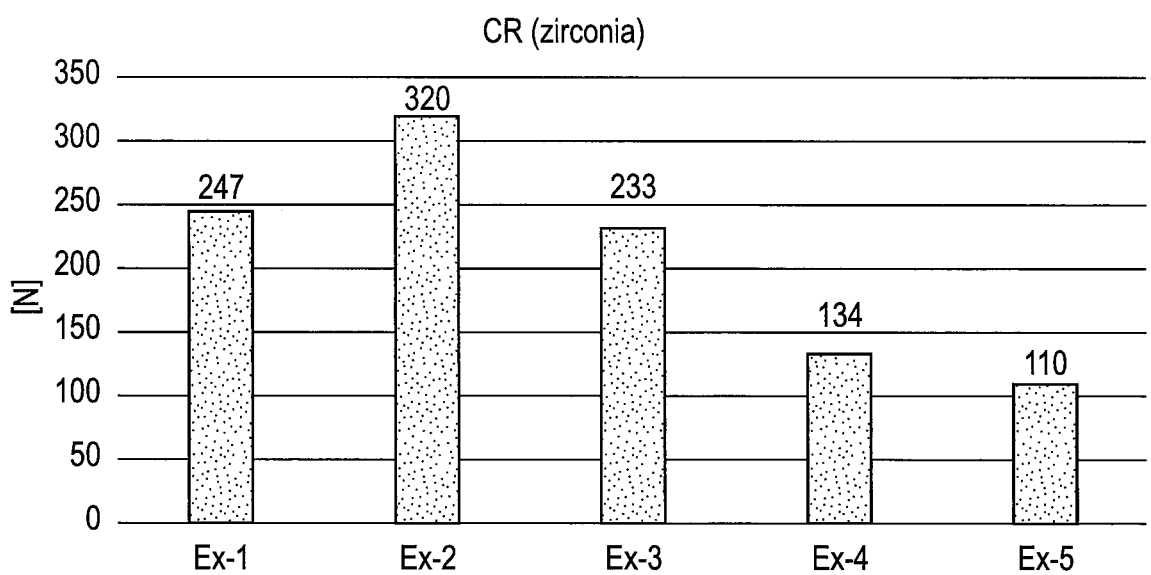
Figure 6:
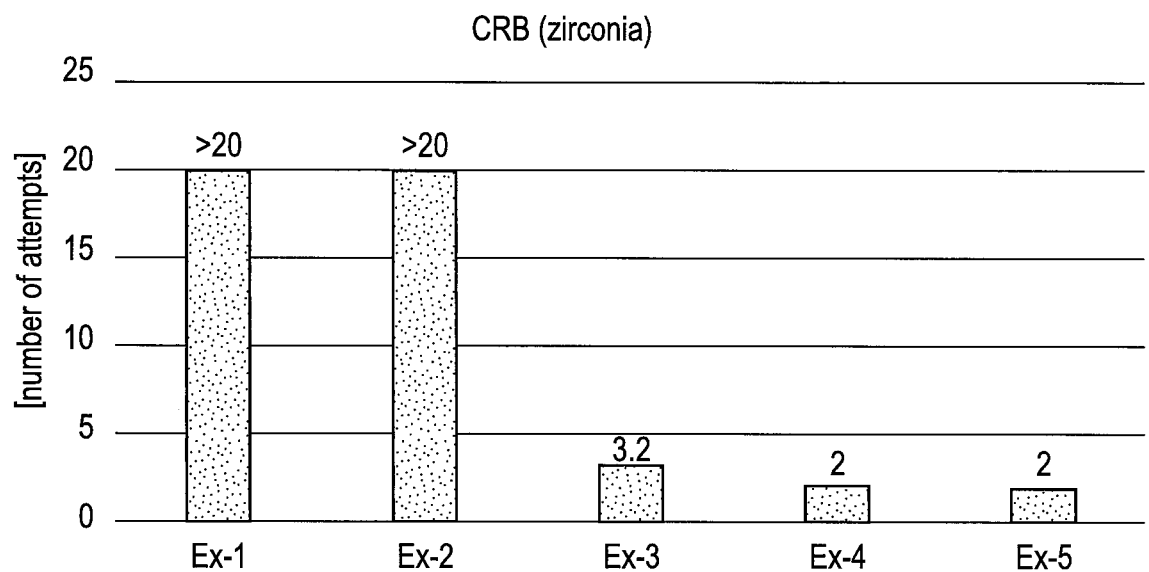
Figure 7:
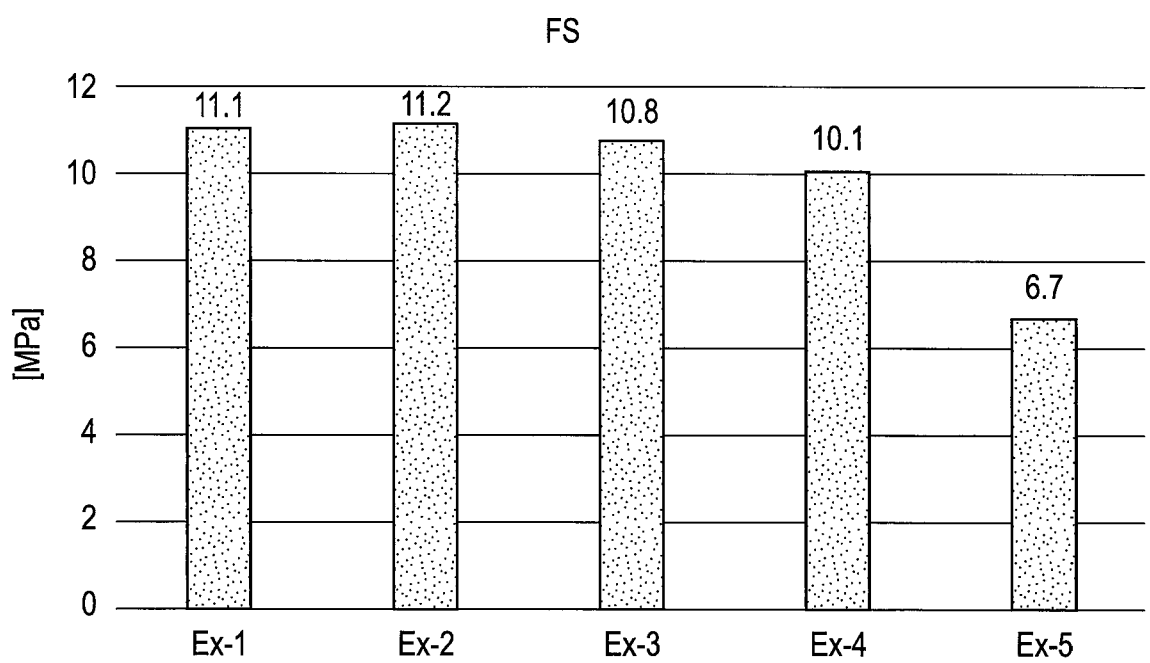
FIGS. 7 and 8 show the evolution of flexural- and compressive strength according to changes in the overall cement formulation (cf. tables 1, 2 and 4). Specifically.
Figure 8:
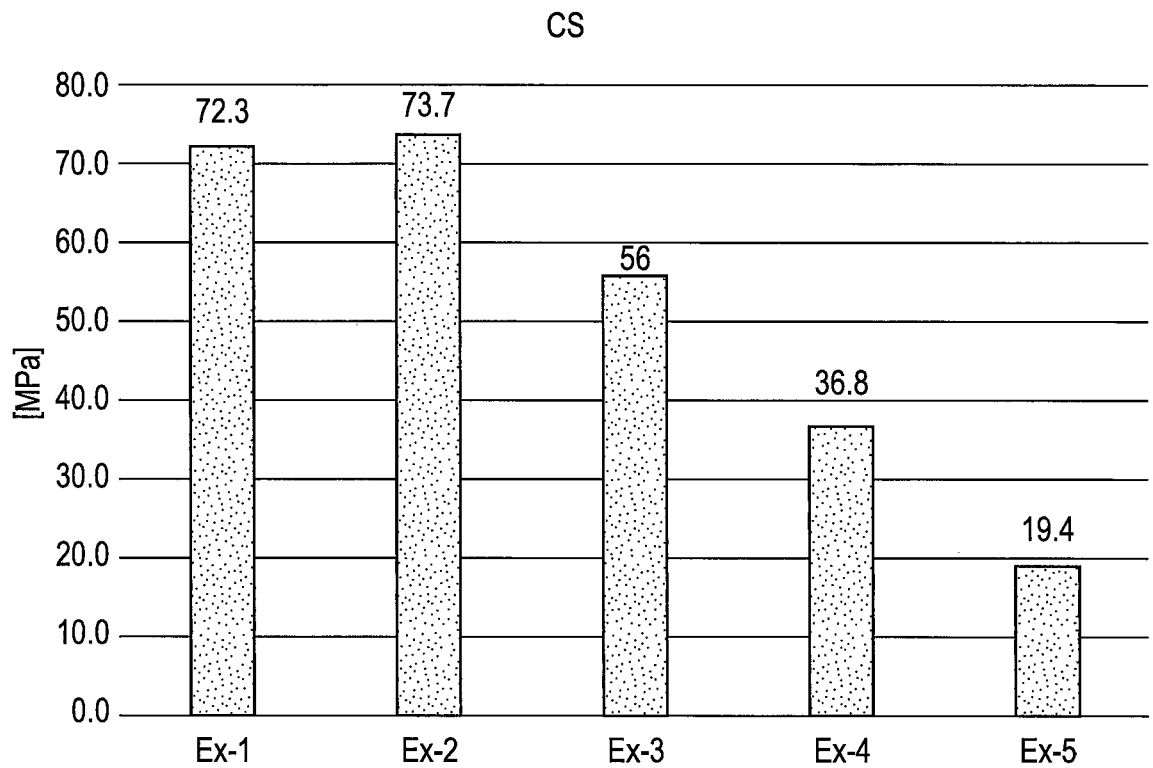
Figure 9:
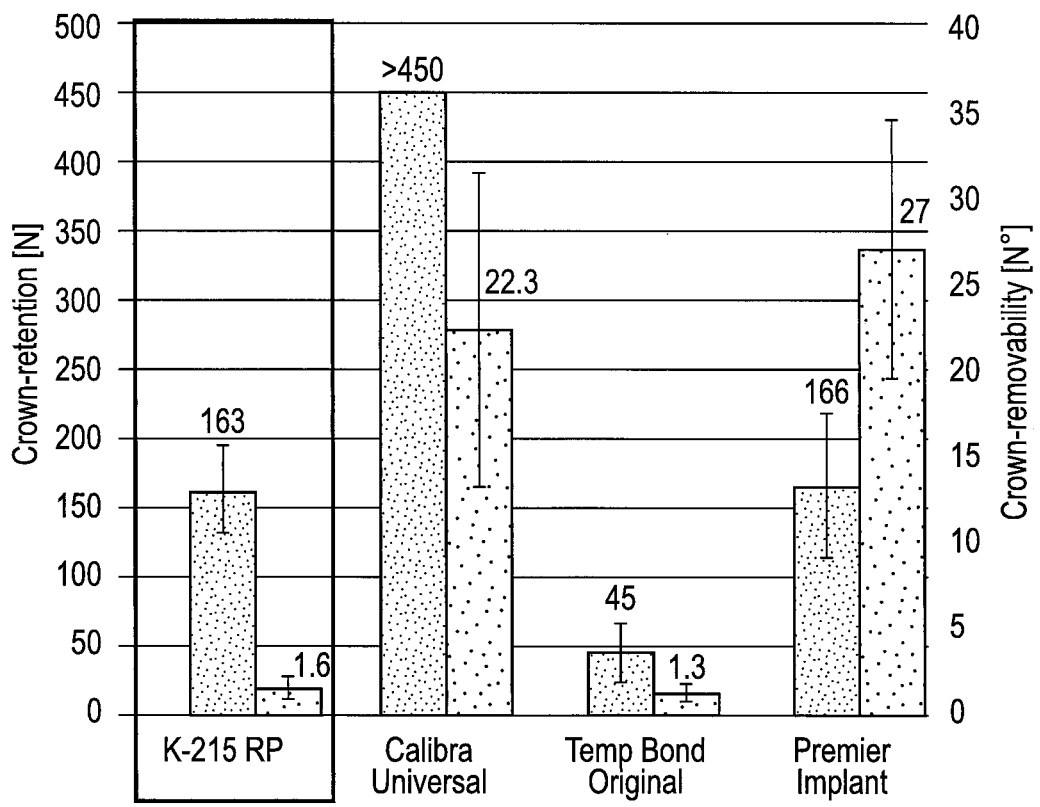
FIGS. 9 to 14 show a comparison between a resin modified dental luting cement composition according to Ex-3 of the present invention and commercial luting cements with regard to physical properties.
Figure 10:
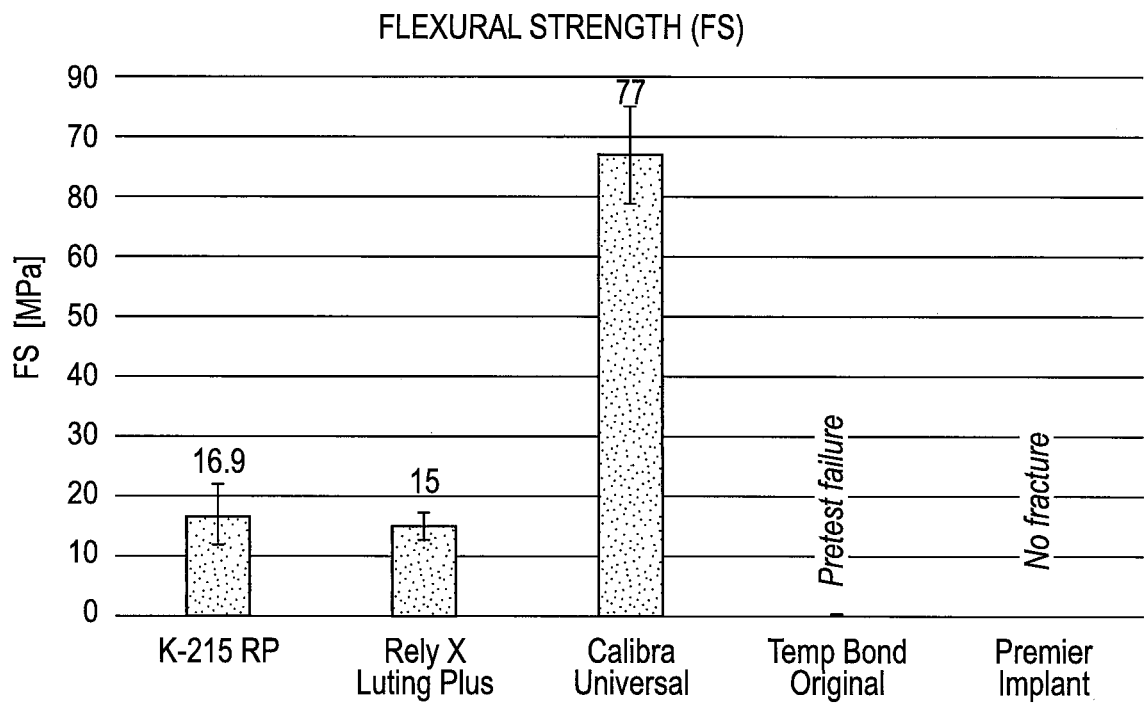
Figure 11:
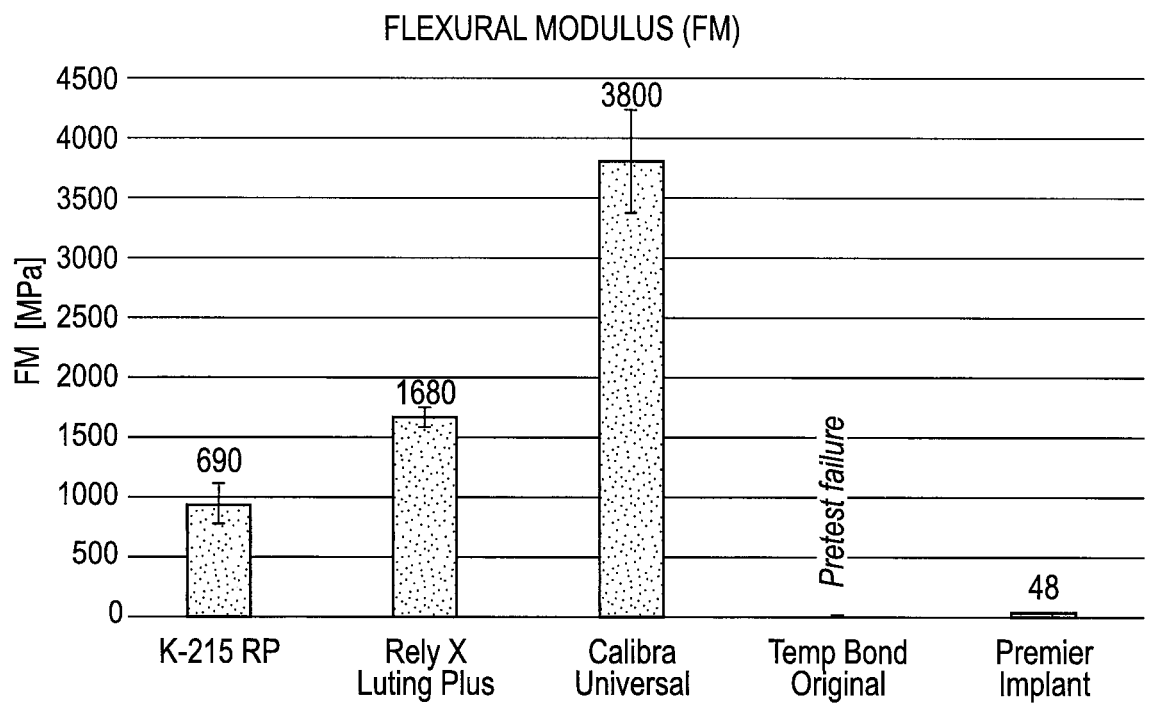
Figure 12:
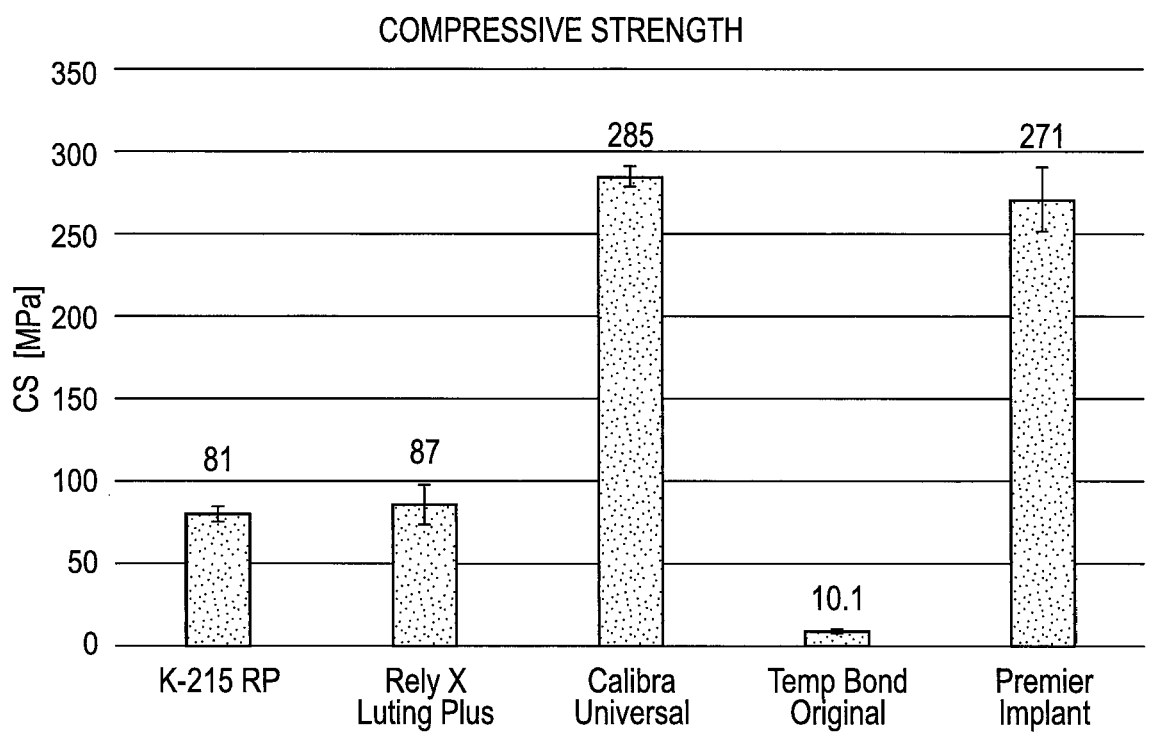
Figure 13:
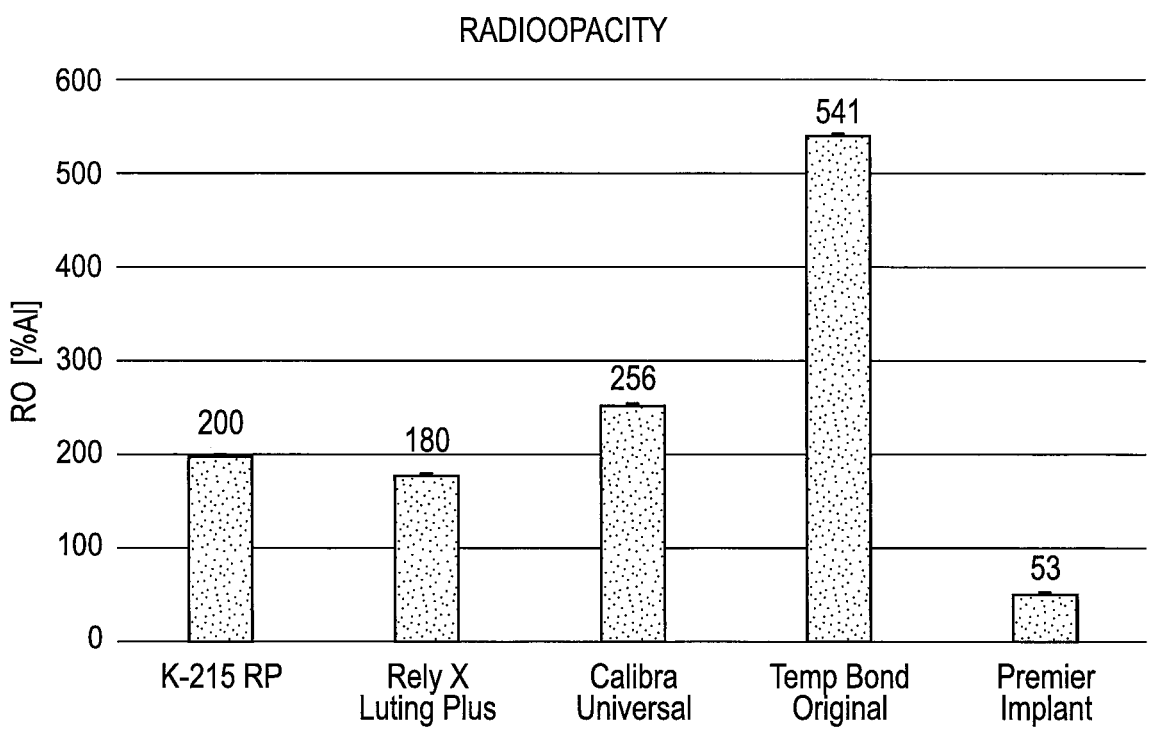
Figure 14:
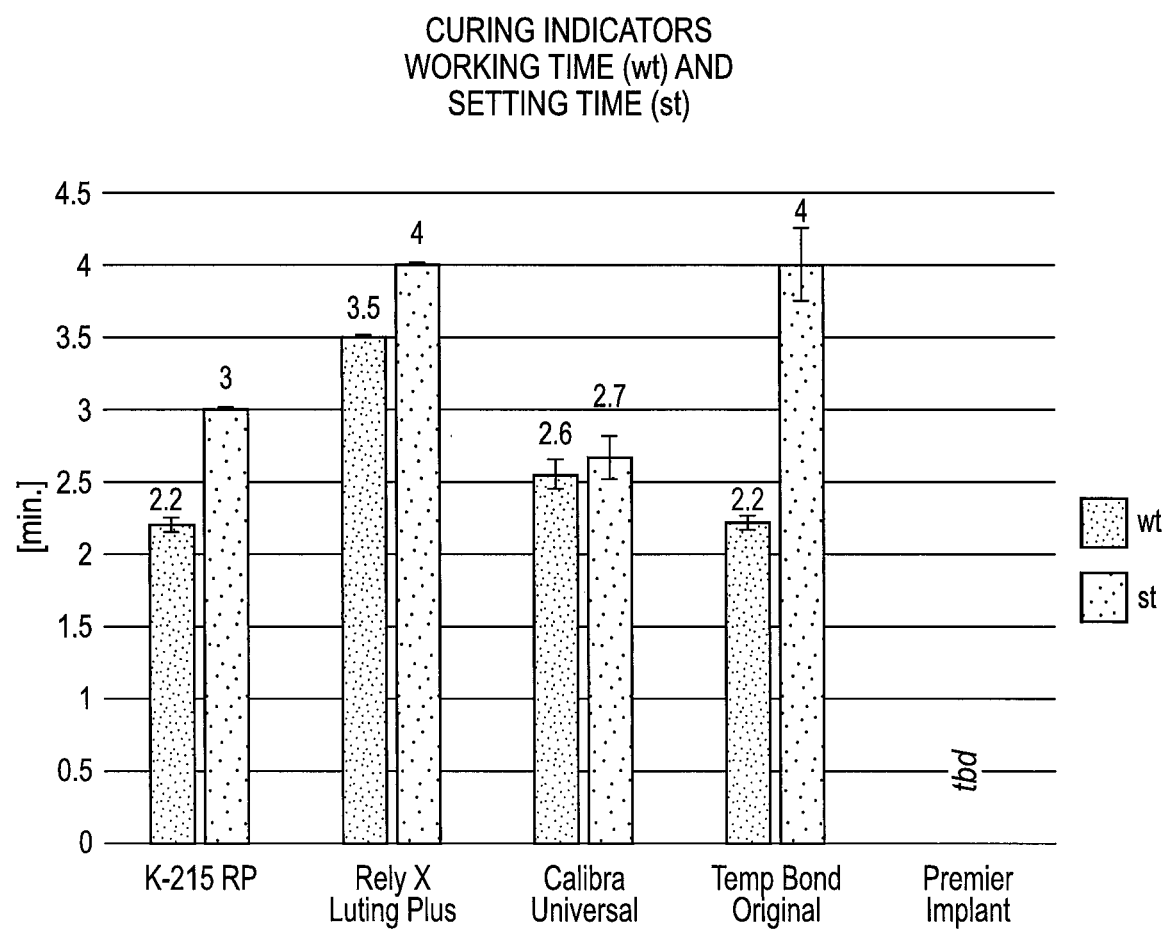
Figure 15:
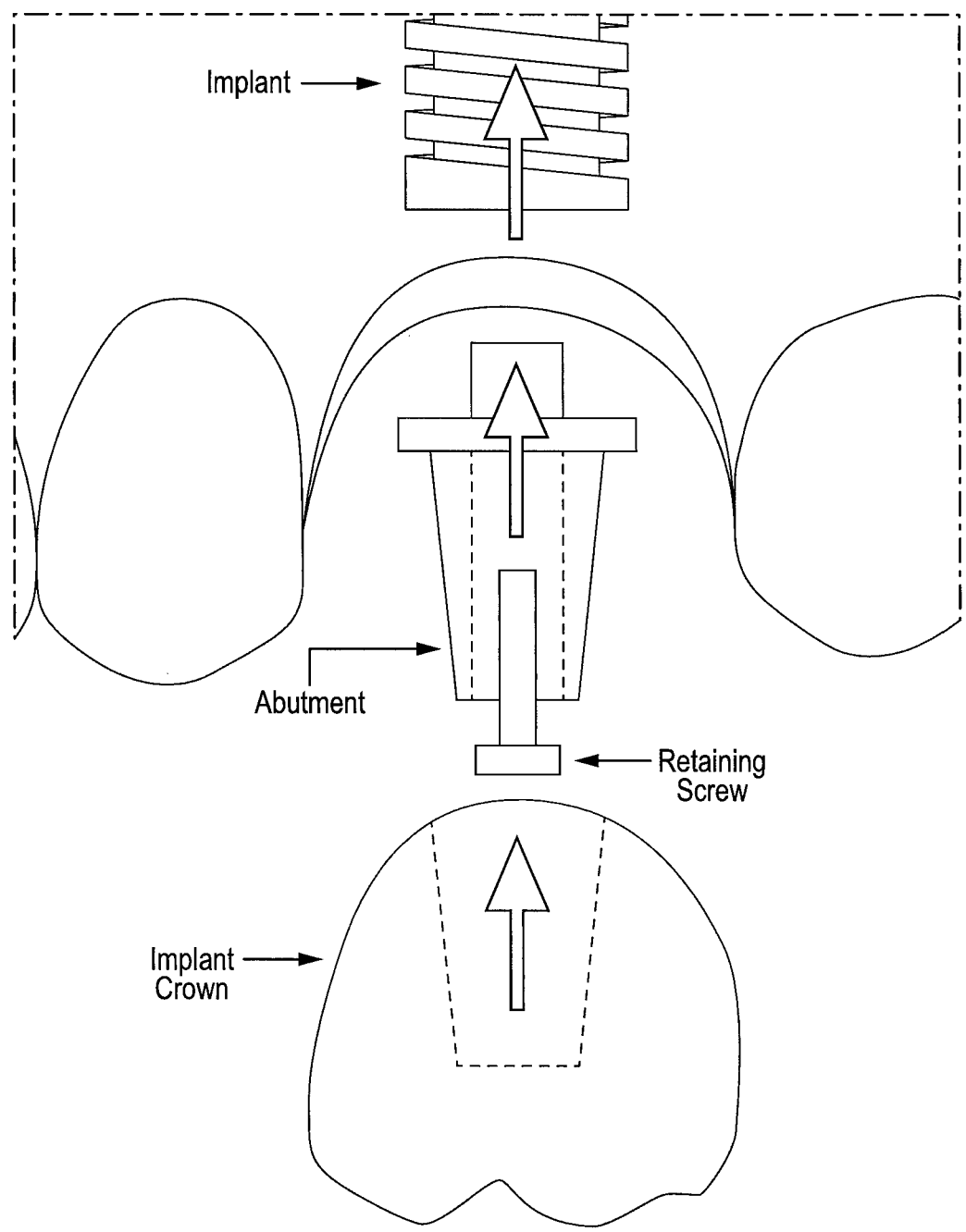
FIG. 15 shows a schematic representation and interaction of elements involved in connecting prosthetics to abutments by an implant cement.

The terms "polymerization" and "polymerizable" relates to the combining or the capability to combine by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as polymer networks. In case of a higher conversion rate of the polymerizable monomer, the amount of multifunctional monomers may be reduced or the leaching problem may be alleviated.

In this description, unless otherwise specified, a halogen atom denotes a fluorine atom, a chlorine atom, a bromine atom or a iodine atom. An alkyl group denotes, for example, a straight-chain or branched-chain $C_{1-16}$ alkyl group, in particular a $C_{1-4}$ alkyl group. Examples for an alkyl group include methyl, ethyl, propyl, isopropyl, butyl, sec-butyl, isobutyl, tert-butyl, pentyl, hexyl and octyl. A fluoroalkyl group denotes, for example, a straight-chain or branched-chain fluorinated $C_{1-4}$ alkyl group, which may be perfluorinated or contain (2x) fluorine atoms, wherein x is the carbon number of the fluoroalkyl group. A cycloalkyl group denotes a $C_{3-6}$ cycloalkyl group such as cyclopropyl, cyclobutyl, cyclopentyl and cyclohexyl. An aryl group denotes a $C_{6-14}$ aryl group such as phenyl, naphthyl.

The present invention provides a resin modified dental luting cement composition. Preferably, the resin modified dental luting cement composition is a resin modified dental implant cement composition. Preferably, the resin modified dental luting cement composition according to the present invention further comprises a photoinitiator and/or an antibacterial agent.

Preferably, the resin modified dental luting cement composition according to the present invention has a crown retention when cured as measured according to the present description of at least 140 N, more preferably at least 150 N. Moreover, the resin modified dental luting cement composition according to the present invention has a crown-removability of preferably at most at most 5 attempts, more preferably at most 3, and still more preferably at most 2 on average as measured according to the present description.

Preferably, the resin modified dental luting cement composition according to the present invention has a compressive strength when cured of at least 45 MPa, more preferably at least 50 MPa.

Preferably, the resin modified dental luting cement composition according to the present invention has a flexural strength when cured of at least 10, more preferably at least 12 MPa.

Accordingly, the covalent network (A), the ionic network (B), and an inert filler (C) of the resin modified dental luting cement composition according to the present invention may be present in a ratio of 0.5 to 1.5:1.0:0.05 to 1.5. According to a particular preferred embodiment, (A) is present in a proportion of 20 to 30 wt. %, more preferably 22 to 28 wt. %, (B) is present in a proportion of 35 to 45 wt. %, more preferably 37 to 43 wt. % and (C) is present in a proportion of 30 to 40 wt. %, more preferably 32 to 38 wt. % based on the total weight of the cured composition.

The Polymerizable Resin Component (a)

The resin modified dental luting cement composition comprises a polymerizable resin component.

According to a preferred embodiment, the polymerizable resin component comprises a compound of the following formula (I):

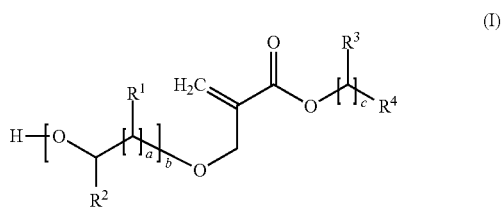

wherein
$R^1$ and $R^2$ which may be the same or different, independently represent a hydrogen atom or a $C_{1-6}$ alkyl group or a $C_{1-6}$ fluoroalkyl group;
$R^3$ which may the same or different when more than one $R^3$ is present, independently represent a hydrogen atom or a $C_{1-6}$ alkyl group or a $C_{1-6}$ fluoroalkyl group;
$R^4$ represents a hydrogen atom or a $C_{1-6}$ alkyl group or a $C_{1-6}$ fluoroalkyl group;
a is an integer of from 1 to 4;
b is 0 or an integer of from 1 to 9; and
c is 0 or an integer of from 1 to 9.

In formula (I), $R^1$ and $R^2$ may be the same or different. In case more than one $R^1$ is present in a compound of formula (I), the more than one $R^1$ may be the same or different. In case more than one $R^2$ is present in a compound of formula (I), the more than one $R^2$ may be the same or different. In each case, $R^1$ and $R^2$ independently represent a hydrogen atom or a $C_{1-6}$ alkyl group or a $C_{1-6}$ fluoroalkyl group. Preferably, $R^1$ and $R^2$ are a hydrogen atom, a methyl group or an ethyl group.

In formula (I), one or more and up to c $R^3$ may be present. In case more than one $R^3$ is present, the more than one $R^3$ may be the same or different. $R^3$ represents a hydrogen atom or a $C_{1-6}$ alkyl group or a 01-6 fluoroalkyl group. Preferably, $R^3$ represents a hydrogen atom or a methyl group.

In formula (I), $R^4$ represents a hydrogen atom or a $C_{1-6}$ alkyl group or a $C_{1-6}$ fluoroalkyl group. Preferably, $R^4$ represents a hydrogen atom or a $C_{1-4}$ alkyl group.

In formula (I), a is an integer of from 1 to 4. Preferably, a is 1 or 2.

In formula (I), b is 0 or an integer of from 1 to 9. Preferably, b is 0, 1, 2 or 3.

In formula (I), c is 0 or an integer of from 1 to 9. Preferably, c is 0, 1, 2, 3, 4, 5, or 6.

More preferably, the polymerizable resin component comprises a compound of the following formula (II):

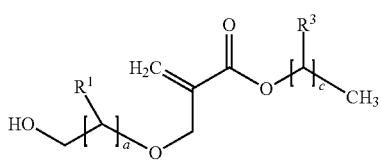

wherein
$R^1$ and $R^3$
which may be the same or different, independently represent a hydrogen atom, a $C_{1-4}$ alkyl group or a $C_{1-4}$ fluoroalkyl group;
a is an integer of from 1 to 4; and
c is 0 or an integer of from 1 to 9.

Preferably, $R^1$ and $R^3$ are hydrogen atoms. Moreover, a is preferably 1, 2 or 3. Furthermore, c is preferably 1, 2 or 3.

The most preferred compound of formula (I) is 2-[2-hydroxyethoxy)-methyl]acrylicacid ethylester (HMAE) (ethyl 2-[4-hydroxy-2-oxabutyl]acrylate) of the following formula.

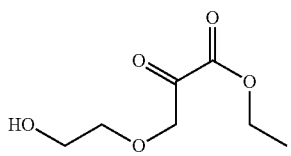

HMAE may be prepared according to the procedure of example 1 of EP1601679.

A compound of formula (I), notably HMAE, is able to replace HEMA and bis-GMA in a generic composition and thereby avoids discoloration problems and biocompatibility problems. Moreover, a compound of formula (I), notably HMAE, facilitates the dispersion of pastes when a generic resin modified dental luting cement composition is prepared. Also, it was found that a compound of formula (I), notably HMAE, provides increased compressive strength and flexural strength when used to replace HEMA in a generic composition. Finally, a compound of formula (I), notably HMAE, was found to provide at the same time high crown retention and easy crown removability when used in a composition according to the present invention.

Alternatively or additionally, the polymerizable resin component may contain polymerizable compound of the following formula (III):

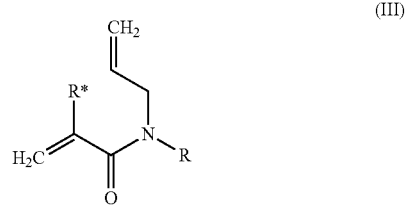

wherein
R represents a straight chain or branched $C_{2-18}$ alkyl or alkenyl group, which may be substituted by a group selected from a hydroxyl group, a $C_{1-4}$ alkoxy group, a tertiary amino group, and a carboxyl group, and wherein 1 to 8 carbon atoms in the main chain of the $C_{2-18}$ alkyl or alkenyl group may independently from each other be replaced by a heteroatom selected from an oxygen atom and a sulfur atom, and
R* represents a hydrogen atom or a methyl group.

A polymerizable compound of formula (III) has low dynamic viscosity of preferably at most 10 Pa·s at 23° C. Accordingly, processing of the compound as such as well as handling of a dental composition comprising the polymerizable compound of formula (III) are excellent. Furthermore, a polymerizable compound of formula (III) has high reactivity in terms of polymerization enthalpy-$\Delta R_H$, which is preferably about 50 to 75 kJ/mol. Finally, the polymerizable compound of formula (III) has an excellent hydrolysis stability. The polymerizable compounds of formula (III) may be used as reactive diluent(s) for reducing the dynamic viscosity of a high-viscosity dental composition.

In formula (III), the term "tertiary amino group" in the definition of R of formula (III) means an amino group substituted with two groups which may be the same or different and which are independently selected from $C_{1-4}$ alkyl groups, preferably a methyl group.

It is preferred that R is a group of the following formula (IV)

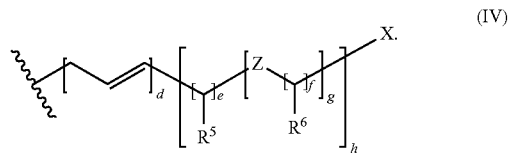

In formula (IV), X is a hydrogen atom, a hydroxyl group, a $C_{1-4}$ alkoxy group, a tertiary amino group or a carboxyl group, and Z is an oxygen atom or a sulfur atom, and in case more than one Z is present, the Z may be the same or different. $R^5$ is a hydrogen atom or a group selected from a hydroxyl group, a $C_{1-4}$ alkyl group, a $C_{1-4}$ alkoxy group, a tertiary amino group, and a carboxyl group. In case more than one group $R^5$ is present, the groups may be the same or different. $R^6$ is a hydrogen atom or a group selected from a hydroxyl group, a $C_{1-4}$ alkyl group, a $C_{1-4}$ alkoxy group, a tertiary amino group, and a carboxyl group. In case more than one group $R^6$ is present, the groups may be the same or different.

In formula (IV), d is 0 or 1, e is an integer of from 2 to 18, f is an integer of from 2 to 16, g is an integer of from 0 to 8, and his an integer of from 1 to 3.

If "d" in formula (IV) is 1, then R contains a single allylic moiety —[H2C—CH=CH]—, which is attached to the nitrogen atom of the N-allyl (meth)acrylamide group of formula (III). If "d" in formula (IV) is 0, then R does not contain an allylic moiety.

Preferably, in formula (IV), d is 0 or 1, b is an integer of from 2 to 12, e is an integer from 2 to 8, f is an integer from 0 to 8, and g is 1 or 2. More preferably, in formula (II), d is 0 or 1, e is an integer of from 2 to 9, f is an integer from 2 to 4, g is an integer from 0 to 2 and 5 to 8, and h is 1 or 2. Most preferably, in formula (II), d is 0 or 1, e is an integer of from 2 to 6, f is 2, g is 0 or an integer of from 5 to 8, and h is 1.

Preferably, the polymerizable compound of formula (III) is selected from the following structural formulae (V) or (VI):

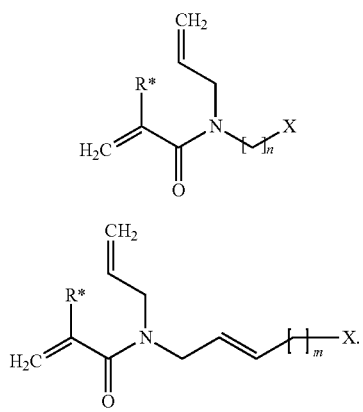

In formulae (V) and (VI), R* represents a hydrogen atom or a methyl group, preferably a hydrogen atom, X is a hydrogen atom, a hydroxyl group, a tertiary amino group or a carboxyl group, n is an integer of from 5 to 18, and m is an integer of from 2 to 15.

Preferably, in the compound of formula (V), n is 6 to 12, and in the compound of the formula (VI), n is 2 to 8.

Compounds of formula (VI) are preferred, since they contain a double bond imparting C—H acidity to the hydrogen atom of the adjacent moiety —CH—N-allyl. Without wishing to be bound to theory, it is believed that this C—H acidity, in combination with the polymerizable C=C double bond of the (meth)acryl group provides for the particularly advantageous polymerization enthalpy and viscosity of compound of formula (VI). In addition, owing to the above described C—H acidity, the compound of formula (VI) may provide an advantageous maximum rate of polymerization and desirable mechanical characteristic such as flexural strength.

Particular preferred compounds of formula (III) have the following structural formulae:

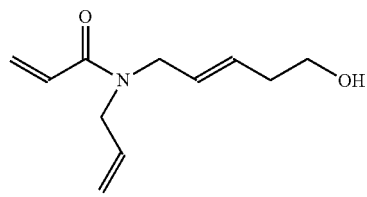

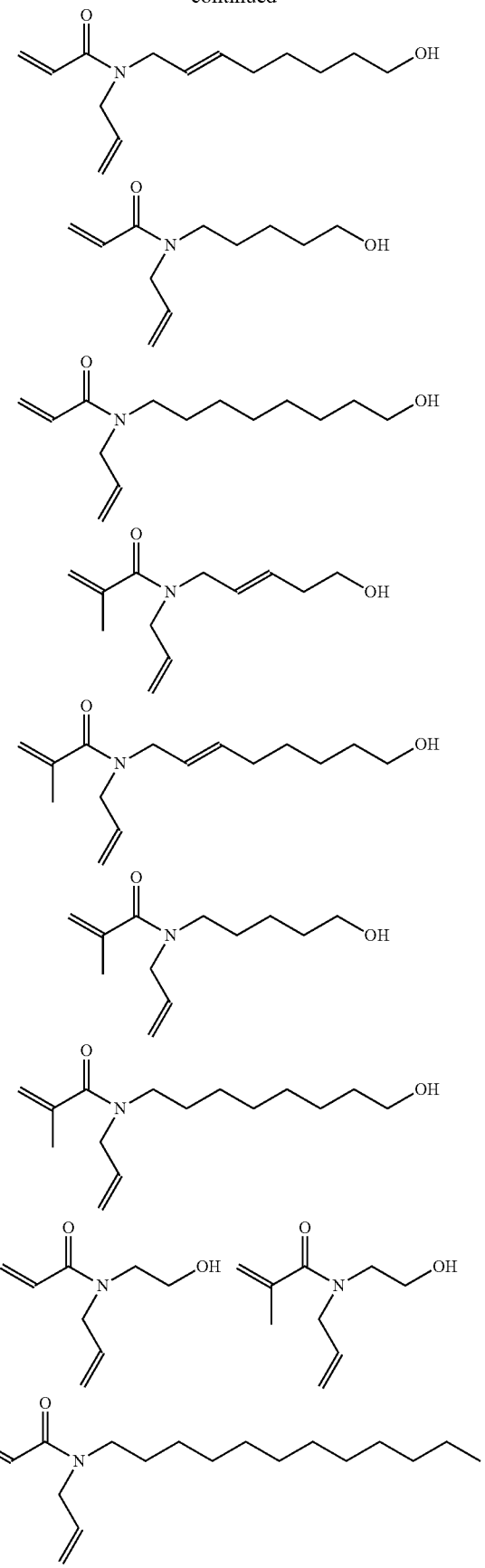

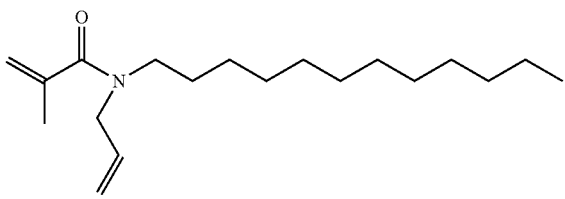
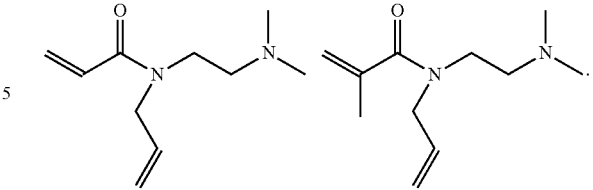

From the particularly preferred polymerizable compounds of formula (III) shown above, the acryloyl compounds are most preferred.

A compound of formula (III) may be prepared by using the method as disclosed in M. Porel et al., Journal of the American Chemical Society, 2014, 136, pages 13162 to 13165, or as described in EP 16 204 000.0.

Suitable further compounds for the polymerizable resin component are alpha,beta unsaturated monomers for providing altered properties such as toughness, adhesion, and set time. Such alpha,beta-unsaturated monomers may be acrylates and methacrylates such as methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, 2-propenoic acid 2-methyl 1,1'-[(1-methylethylidene) bis[4,1-phenyleneoxy(2-hydroxy-3,1-propanediyl)]]ester also termed bisphenol A glycerolate dimethacrylat ("bis-GMA", CAS-No. 1565-94-2), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl) propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acryalte]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates. Mixtures of alpha,beta-unsaturated monomers can be added if desired.

Alternatively or additionally, the polymerizable resin component may contain N,N'-(2E)-but-2-en-1,4-diallylbis-RN-prop-2-en-1) amide (BAABE), N,N'-diethyl-1,3-bisacrylamido-propan (BADEP), 1,3-bisacrylamido-propan (BAP), 1,3-bisacrylamido-2-ethyl-propan (BAPEN) or N,N-di(allyl acrylamido) propane or a polymerizable compound disclosed in patent publications EP3231411, EP2705827, WO2014040729 and in patent application EP 15 178 515.

Preferably, the resin modified dental luting cement composition comprises based on the total weight of the composition 10 to 30 percent by weight, more preferably 15 to 25 percent by weight of the polymerizable resin component.

Preferably, the resin modified dental luting cement composition according to the present invention does not contain HEMA or bis-GMA.

The Polyacidic Polymer Component (b)

The resin modified dental luting cement composition comprises a polyacidic polymer component. The term "polyacidic" as used with the term "polyacidic polymer component" means that the polymer has a plurality of acidic groups, preferably carboxylic acid groups, which may participate in a cement reaction with a reactive particulate glass. The carboxylic acid groups are preferably present in the backbone and derived from acrylic acid, methacrylic acid and/or itaconic acid. The polyacidic polymer component may be as described in EP3231412.

Preferably, the polyacidic polymer component consists essentially of a polyacrylic acid having an average molecular weight Mw of from 10 to 75 kDa.

Preferably, the resin modified dental luting cement composition comprises based on the total weight of the composition 5 to 20 percent by weight, preferably 8 to 18 percent by weight of the polyacidic polymer component.

The Filler Component (c)

The resin modified dental luting cement composition comprises a filler component.

The filler component comprises a particulate zinc oxide containing filler adapted to be reactive with the polyacidic polymer component in a cement reaction. The particulate zinc oxide containing filler is obtainable by transforming a solid mixture of metal oxides including ZnO by a thermal melt process into a glass followed by milling, which glass is capable of reacting with a polymer containing acidic groups in a cement reaction. The glass is in a particulate form. Moreover, the particulate zinc oxide containing filler may be surface modified, e.g. by silanation or acid treatment. Any conventional particulate zinc oxide containing filler may be used for the purpose of the present invention.

According to a preferred embodiment, the particulate zinc oxide containing filler adapted to be reactive with the polyacidic polymer component in a cement reaction contains silicon, aluminum, zinc, phosphorus and fluorine as essential elements, whereby silicon, aluminum, zinc and phosphorus are contained in the composition predominantly as oxides. Specifically, the reactive particulate glass may comprise
a. 10-35% by weight of silica
b. 10-35% by weight of alumina
c. 3-30% by weight of zinc oxide
d. 4-30% by weight of $P_2O_5$
e. 3-25% by weight of fluoride, Silica (calculated as $SiO_2$) is preferably contained in the glass composition in an amount of from 10-35% by weight. In a more preferred embodiment, silica is contained in an amount of from 20-25% by weight. Alumina (calculated as $Al_2O_3$) is preferably contained in an amount of from 10-35% by weight. In a more preferred embodiment, alumina is contained in an amount of from 20-25% by weight. The weight ratio between silica and alumina is preferably in a range of from 1.2 to 0.8, more preferably in a range of from 1.15 to 1.0.

Zinc oxide (calculated as ZnO) is preferably contained in the glass composition used according to the invention in an amount of from 3-30% by weight. In a more preferred embodiment, zinc oxide is contained in an amount of from 13-18% by weight.

Phosphorus pentoxide (calculated as $P_2O_5$) is preferably contained in the glass composition used according to the invention in an amount of from 4-30% by weight. In a preferred embodiment, phosphorus pentoxide is contained in an amount of from 14 to 18% by weight.

Fluoride is preferably contained in the glass composition according to the invention in an amount of from 3-25% by weight. In a preferred embodiment, fluoride is contained in an amount of from 4-7% by weight.

Besides the preferred essential elements, the particulate glass composition of the present invention may further comprise from 18-21% by weight of calcium oxide plus strontium oxide.

The particulate glass composition preferably essentially does not contain any alkaline metal oxides. In particular, the glass composition contains at most 2% by weight, preferably at most 1.5% by weight, of alkaline metal oxides, $M_2O$, wherein M is Li, Na, or K. In a preferred embodiment, the content of $Na_2O$ in the particulate glass is less than 1% by weight.

The particulate zinc oxide containing filler usually has a mean particle size of from 0.1 to 10 μm, preferably of from 1 to 8 μm as measured, for example, by electron microscopy or by using a conventional laser diffraction particle sizing method as embodied by a MALVERN Mastersizer S or MALVERN Mastersizer 2000 apparatus.

The particulate zinc oxide containing filler may have a unimodal or multimodal (e.g., bimodal) particle size distribution, wherein a multimodal reactive particulate glass represents a mixture of two or more particulate fractions having different average particle sizes.

The particulate zinc oxide containing filler may be a an agglomerated reactive particulate glass which is obtainable by agglomerating a reactive particulate glass in the presence of a modified polyacid and/or polymerizable (meth)acrylate resins. The particle size of the agglomerated reactive particulate glass may be adjusted by suitable size-reduction processes such as milling.

The particulate zinc oxide containing filler may alternatively or additionally be surface modified by a surface modifying agent. Preferably, the surface modifying agent is a silane.

The filler component further comprises an inert particulate filler which cannot react with the polyacidic polymer in a cement reaction.

The inert particulate filler may be included for changing the appearance of the composition, for controlling viscosity of the composition, for modulating mechanical strength, and e.g. for imparting radiopacity. The non-reactive filler should be non-toxic and suitable for use in the mouth. The filler may be in the form of an inorganic material. It can also be a crosslinked organic material that is insoluble in the polymerizable polymer and is optionally filled with inorganic filler.

For example, a suitable inert particulate inorganic filler may be selected from quartz, a nitride such as silicon nitride, colloidal silica, submicron silica such as pyrogenic silicas, colloidal zirconia, feldspar, borosilicate glass, kaolin, talc, a metal fluoride such as ytterbium fluoride, or a metallic powder comprising one or more metals or metal alloys.

A preferred inert particulate inorganic filler is AEROSIL® OX 50 (Evonic Industries).

Examples of suitable inert organic fillers include filled or unfilled particulate PMMA, polycarbonates or polyepoxides. Preferably the surface of the non-reactive organic filler particles is treated with a coupling agent in order to enhance the bond between the filler and the matrix. Suitable coupling agents include silane compounds such as gamma-methacryloxypropyltrimethoxysilane, gamma-mercaptopropyltriethoxysilane and gamma-aminopropyltrimethoxysilane.

The inert particulate filler may have a unimodal or polymodal (e.g., bimodal) particle size distribution, wherein the particulate filler preferably has an mean particle size of from 0.001 to 100 μm, preferably of from 5 nm to 60 μm.

The BET surface area [$m^2/g$] of the inert particulate filler may be from 10 to 300 $m^2/g$, more preferably from 20 to 50 $m^2/g$.

The particle size may be measured, for example, by electron microscopy or by using a conventional laser diffraction particle sizing method as embodied by a MALVERN Mastersizer S or MALVERN Mastersizer 3000 apparatus. The particulate filler may be a multimodal particulate non-reactive filler representing a mixture of two or more particulate fractions having different average particle sizes. The particulate reactive filler may also be a mixture of particles of different chemical composition. The particulate non-reactive filler may be surface modified by a surface modifying agent.

Moreover, the inert particular filler preferably comprises a radiopaque filler and a nanofiller.

According to a preferred embodiment, the resin modified dental luting cement composition according to the present invention comprises based on the total weight of the composition 35 to 65 percent by weight, more preferably 40 to 60 percent by weight of the filler component comprising a particulate zinc oxide containing filler adapted to be reactive with the polyacidic polymer component in a cement reaction and an inert particulate filler which cannot react with the polyacidic polymer in a cement reaction.

The Redox Initiator System (d)

The resin modified dental luting cement composition comprises a redox initiator system for initiating polymerization of the polymerizable resin component, which comprises an oxidizing agent and a reducing agent.

The dental composition according to the present invention comprises a redox polymerization initiator system. The initiator system may additionally contain a photoinitiator.

The amount of reducing agent and oxidizing agent should be sufficient to provide the desired degree of polymerization. Preferably, the mixed but unset cements of the invention contain a combined weight of about 0.01 to about 10%, more preferably about 0.2 to about 5%, and most preferably about 0.3 to about 3% of the reducing agent and oxidizing agent, based on the total weight (including water) of the mixed but unset cement components. The reducing agent or the oxidizing agent can be microencapsulated as described in U.S. Pat. No. 5,154,762. This will generally enhance shelf stability of the cement parts and if necessary permit packaging both the reducing agent and oxidizing agent together. Water-soluble and water-insoluble encapsulants can be employed. Suitable encapsulating materials include cellulosic materials as cellulose acetate, cellulose acetate butyrate, ethyl cellulose, hydroxymethyl cellulose and hydroxyethyl cellulose being preferred. Other encapsulants include polystyrene, copolymers of polystyrene with other vinylic monomers and polymethylmethacrylate, copolymers of methylmethacrylate with other ethylenically-unsaturated monomers. Preferred encapsulants are ethylcellulose and cellulose acetate butyrate. By varying the choice of encapsulant and the encapsulation conditions, the onset of curing can be tailored to start at times ranging from seconds to minutes. The ratio of amount of encapsulant to activator generally ranges from 0.5 to about 10 and preferably from about 2 to about 6.

Suitable oxidizing agents (initiators) include peroxides such as benzoyl peroxide, cumene hydroperoxide (CHP), and tert-butyl hydroperoxide, ferric chloride, hydroxylamine (depending upon the choice of reducing agent), perboric acid and its salts, and salts of a permanganate or persulfate anion. Preferred oxidizing agents are peroxides, potassium persulfate, ammonium persulfate and hydrogen peroxide.

Suitable reducing agents (activators) include ascorbic acid, a thiourea compound such as benzyl thiourea, ferrous chloride, ferrous sulfate, hydrazine, hydroxylamine (depending upon the choice of oxidizing agent) oxalic acid, thiourea, and salts of a dithionite or sulfite anion. Preferred reducing agents include a thiourea compound such as benzoylthiourea.

According to a preferred embodiment, the oxidizing agent is a peroxide or hydroperoxide, and/or the reducing agent is a thiourea compound.

According to a preferred embodiment, the resin modified dental luting cement composition according to the present invention comprises based on the total weight of the composition 0.5 to 5 percent by weight, more preferably 0.7 to 4 percent by weight of a polymerization initiator system for initiating polymerization of the polymerizable resin component.

The Water Component (e)

The resin modified dental luting cement composition comprises water. According to a preferred embodiment, the resin modified dental luting cement composition according to the present invention comprises based on the total weight of the composition 10 to 30 percent by weight, more preferably 15 to 25 percent by weight of water.

According to a preferred embodiment, the resin modified dental luting cement composition according to the present invention, which comprises based on the total weight of the composition
(a) 10 to 30 percent by weight of the polymerizable resin component;
(b) 5 to 20 percent by weight of the polyacidic polymer component;
(c) 35 to 65 percent by weight of the filler component comprising a particulate zinc oxide containing filler adapted to be reactive with the polyacidic polymer component in a cement reaction and an inert particulate filler which cannot react with the polyacidic polymer in a cement reaction;
(d) 0.5 to 5 percent by weight of a polymerization initiator system for initiating polymerization of the polymerizable resin component.
(e) 10 to 30 percent by weight of water.

The resin modified dental luting cement composition according to the present invention may also include a retarding or modifying agent such as tartaric acid, for adjusting the working time and a setting time, respectively, when preparing the cement as described in U.S. Pat. Nos. 4,089,830, 4,209,434, 4,317,681 and 4,374,936. In general, an increase in working time results in an increase in setting time as well. The "working time" is the time between the beginning of the setting reaction when the ionomer and modified particulate reactive filler are combined in the presence of water, and the time the setting reaction proceeds to the point when it is no longer practical to perform further physical work upon the system, e.g. spatulate it or reshape it, for its intended dental or medical application. The "setting time" is the time measured from the beginning of the setting reaction in a restoration to the time sufficient hardening has occurred to allow subsequent clinical or surgical procedures to be performed on the surface of the restoration.

In the setting reaction, the particulate reactive glass behaves like a base and reacts with the acidic ionomer to form a metal polysalt which acts as the binding matrix (Prosser, J. Chem. Tech. Biotechnol. 29: 69-87(1979)). Moreover, due to the presence of polymerizable groups, a further crosslinking takes place. Thereby the bonding within the cement does not only rely on ionic salt bridges, but also on covalent and complex bonding. The setting reaction is therefore characterized as a dual chemical cure system that proceeds automatically in the presence of water. The cement sets to a gel-like state within a few minutes and rapidly hardens to develop strength.

The dental composition is a multi-pack, preferably a two-pack composition. The composition may be a paste/paste system, a powder/liquid system, or a liquid/paste system. The composition is designed so as to avoid premature curing of the components. For this purpose, the reactive inorganic filler component and any acid group containing component must be formulated so as to avoid a premature cement reaction. In a first embodiment, the reactive inorganic glass is contained in a first pack and any acid group containing component is contained in a second pack. The first pack may be a powder or a paste. The second pack may be a liquid or paste. In a second embodiment, the first pack is a powder comprising the reactive inorganic filler and a solid polyacidic polymer such as polyacrylic acid, and the second pack is a paste or liquid and contains a further acid group containing component.

The ratio of powder to liquid affects the workability of the mixed ionomer cement systems. Weight ratios higher than 20:1 tend to exhibit poor workability, while ratios below 1:1 tend to exhibit poor mechanical properties, e.g., strength, and hence are not preferred. Preferred ratios are on the order of about 1:3 to about 6:1 and preferably about 1:1 to 4:1.

According to a preferred embodiment, the resin modified dental luting cement composition according to the present invention is a paste/paste composition consisting of a non-aqueous neutral paste and an aqueous acidic paste. Preferably, the neutral paste contains the polymerizable resin component, the particulate zinc oxide containing filler adapted to be reactive with the polyacidic polymer component in a cement reaction, the oxidizing or reducing agent, and optionally inert particulate filler, and wherein the acidic paste contains the polyacidic polymer component, a reducing or oxidizing agent, water and optionally inert particulate filler.

The resin modified dental luting cement composition is preferably packaged in a two-barrel syringe or in a single use two-chamber unit.

The present invention also provides a use of the resin modified dental luting cement composition according to the present invention for adhering an implant restoration to an abutment.

The present invention also provides a use of a compound of the following formula (I):

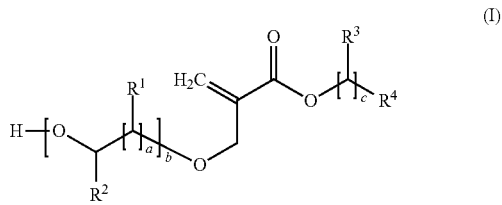

wherein
$R^1$ and $R^2$
which may be the same or different, independently represent a hydrogen atom or a $C_{1-6}$ alkyl group or a $C_{1-6}$ fluoroalkyl group;
$R^3$ which may the same or different when more than one $R^3$ is present, independently represent a hydrogen atom or a $C_{1-6}$ alkyl group or a $C_{1-6}$ fluoroalkyl group;
$R^4$ represents a hydrogen atom or a $C_{1-6}$ alkyl group or a $C_{1-6}$ fluoroalkyl group;
a is an integer of from 1 to 4;
b is 0 or an integer of from 1 to 9; and
c is 0 or an integer of from 1 to 9,
for preparing a dental cement composition.

Preferably, the dental cement composition is a luting cement, more preferably an implant cement. Preferably, the implant cement does not contain HEMA or bis-GMA.

EXAMPLES

Abbreviations:
AHPMA—3-(Acryloyloxy)-2-hydroxypropyl methacrylate
BADEP—1,3-Bis(acrylamido)-N,N'-diethyl-propane
CA—Contact angle
CR—Crown-retention
CRB—Crown-removability
CS—Compressive strength
FS—Flexural strength
FM—flexural modulus
HEMA—2-Hydroxyethyl methacrylate
HMAE—2-[2-hydroxyethoxyymethyl]acrylicacid-ethyl-ester PAA—Poly(acrylic acid) (Mw=30 kDa)
PEM-360—Poly(ethylene glycol) methacrylate (Mn=360 g/mol)
Reactive zinc filler A—Zinc glass, etched
Reactive zinc filler B—Zinc glass, blended with ZnO and MgO
UDMA—2-Propenoic acid, 2-methyl-, 7,7,9(or 7,9,9)-trimethyl-4,13-dioxo-3,14-dioxa-5,12-diazahexadecane-1,16-diyl ester Methods:

Compressive Strength (CS)

Compressive strength was measured according to ISO 9917-1.

Contact Angle (CA)

Contact angle measurements (advancing) were performed on a OCA 15EC device from DataPhysics.

Crown-Retention (CR):

An Ankylos stock abutment (Ankylos Regular/X, GH 3.0, AO) was screwed onto an Ankylos stock implant (Ankylos C/X, ϕ3.5 mm, length 14 mm) with a maximum force of 15 Ncm. The screw channel was closed using Aquasil Soft Putty (Dentsply Sirona) before the abutment was degreased using acetone. A mock-crown (cf. FIG. 1, overall gap to the abutment: 80 μm) from stainless steel or zirconium oxide (Cercon base, DeguDent) was filled with the tested luting cement and pushed onto the abutment. This assembly was then loaded along the vertical axis with 2.5 kg for 10 min. during which excess cement was removed. The assembly was stored for 24 h at 37° C. and 100% rel. H. before linear retention was measured using a material testing device from Zwick/Roell (initial load 1 N, testing speed 0.5 mm/min.). Each test was repeated at least 5 times.

Crown-Removability (CRB)

Sample preparation was done identical to the measurement of CR. However, instead of using the material testing device for removal of the mock-crowns, a commercially available crown-removal instrument (S—U-Crown-Butler, Schuler-Dental) was used on setting 3 of 3. Each test was repeated at least 5 times.

Flexural Strength/Flexural Modulus (FS/FM)

Flexural strength/-modulus were measured according to ISO 9917-2.

Formulations:

TABLE 1

Formulation of acidic pastes according to the invention

|  | A1 (MAB 2-25-1) | | A2 (MAB 2-25-2) | | A3 (MAB 2-25-3) | | A4 (MAB 2-25-4) | | A5 (MAB 2-25-5) | |
| --- | --- | --- | --- | --- | --- | --- | --- | --- | --- | --- |
|  | [wt.-%] | [g] | [wt.-%] | [g] | [wt.-%] | [g] | [wt.-%] | [g] | [wt.-%] | [g] |
| PAA | 43.22 | 8.64 | 37.80 | 7.56 | 32.76 | 6.55 | 27.71 | 5.54 | 23.40 | 4.68 |
| Distilled water | 32.83 | 6.57 | 38.33 | 7.67 | 43.29 | 8.66 | 48.34 | 9.67 | 52.65 | 10.53 |
| Tartaric acid | 4.63 | 0.93 | 4.63 | 0.93 | 4.63 | 0.93 | 4.63 | 0.93 | 4.63 | 0.93 |
| N-Benzoylthiourea | 1.32 | 0.26 | 1.32 | 0.26 | 1.32 | 0.26 | 1.32 | 0.26 | 1.32 | 0.26 |
| Fumed silica (Ox 50) | 18.00 | 3.60 | 18.00 | 3.60 | 18.00 | 3.60 | 18.00 | 3.60 | 18.00 | 3.60 |
| SUM | 100.00 | 20.00 | 100.00 | 20.00 | 100.00 | 20.00 | 100.00 | 20.00 | 100.00 | 20.00 |

TABLE 2

Formulation of neutral pastes according to the invention

|  | N1 (MAB 2-23-1) | | N2 (MAB 2-23-2) | | N3 (MAB 2-23-3) | | N4 (MAB 2-23-4) | | N5 (MAB 2-23-5) | |
| --- | --- | --- | --- | --- | --- | --- | --- | --- | --- | --- |
|  | [wt.-%] | [g] | [wt.-%] | [g] | [wt.-%] | [g] | [wt.-%] | [g] | [wt.-%] | [g] |
| BADEP | 17.70 | 3.54 | 20.23 | 4.05 | 22.76 | 4.55 | 25.29 | 5.06 | 27.82 | 5.56 |
| HMAE | 6.38 | 1.28 | 7.29 | 1.46 | 8.20 | 1.64 | 9.11 | 1.82 | 10.02 | 2.00 |
| UDMA | 2.72 | 0.54 | 3.11 | 0.62 | 3.50 | 0.70 | 3.89 | 0.78 | 4.28 | 0.86 |
| AHPMA | 0.44 | 0.09 | 0.50 | 0.10 | 0.56 | 0.11 | 0.62 | 0.12 | 0.68 | 0.14 |
| Cumenehydroperoxide | 0.76 | 0.15 | 0.87 | 0.17 | 0.98 | 0.20 | 1.09 | 0.22 | 1.20 | 0.24 |
| Reactive zinc filler A | 31.92 | 6.38 | 29.22 | 5.84 | 26.52 | 5.30 | 23.82 | 4.76 | 21.12 | 4.22 |
| Reactive zinc filler B | 15.40 | 3.08 | 14.10 | 2.82 | 12.80 | 2.56 | 11.50 | 2.30 | 10.19 | 2.04 |
| Ytterbium trifluoride | 19.20 | 3.84 | 19.20 | 3.84 | 19.20 | 3.84 | 19.20 | 3.84 | 19.20 | 3.84 |
| Fumed silica (Ox50, silanized) | 5.48 | 1.10 | 5.48 | 1.10 | 5.48 | 1.10 | 5.48 | 1.10 | 5.48 | 1.10 |
| SUM | 100.00 | 20.00 | 100.00 | 100.00 | 20.00 | 100.00 | 20.00 | 100.00 | 20.00 |

TABLE 3

Formulation of neutral pastes, comparative examples

|  | NC1 (RST 8-14-2) | | NC2 (RST 8-14-1) | | NC3 (AG 21-141-1) | |
| --- | --- | --- | --- | --- | --- | --- |
|  | [wt.-%] | [g] | [wt.-%] | [g] | [wt.-%] | [g] |
| BADEP | 22.76 | 4.55 | 22.76 | 4.55 | 22.76 | 4.55 |
| HMAE | 0.0 | 0.0 | 0.0 | 0.0 | 8.20 | 1.64 |
| HEMA | 8.20 | 1.64 | 0.0 | 0.0 | 0.0 | 0.0 |
| PEM-360 | 0.0 | 0.0 | 8.20 | 1.64 | 0.0 | 0.0 |
| UDMA | 3.50 | 0.70 | 3.50 | 0.70 | 3.50 | 0.70 |
| AHPMA | 0.56 | 0.11 | 0.56 | 0.11 | 0.56 | 0.11 |
| Cumene-hydroperoxide | 0.98 | 0.20 | 0.98 | 0.20 | 0.98 | 0.20 |
| Reactive zinc filler A | 26.52 | 5.30 | 26.52 | 5.30 | 0.0 | 0.0 |

TABLE 3-continued

| Formulation of neutral pastes, comparative examples | | | | | |
|---|---|---|---|---|---|
| | NC1 (RST 8-14-2) | | NC2 (RST 8-14-1) | | NC3 (AG 21-141-1) | |
| | [wt.-%] | [g] | [wt.-%] | [g] | [wt.-%] | [g] |
| Reactive zinc filler B | 12.80 | 2.56 | 12.80 | 2.56 | 39.32 | 7.86 |
| Ytterbium trifluoride | 19.20 | 3.84 | 19.20 | 3.84 | 19.20 | 3.84 |
| Fumed silica (Ox50, silanized) | 5.48 | 1.10 | 5.48 | 1.10 | 5.48 | 1.10 |
| SUM | 100.00 | 20.00 | 100.00 | 20.00 | 100.00 | 20.00 |

Preparation of Acidic- and Neutral Pastes:

Described amounts of components according to tables 1-3 were put in a light-tight plastic container and closed with a lid with a hole in it. Each container was subsequently placed in the SpeedMixer DAC 600-2 VAC-P (Hauschild) and mixed twice at 2500 rpm for 2 min and once at 1000 rpm/100 mbar for 1 min. The hole in the lid was closed with a light-tight scotch tape and containers stored at room temperature until further use.

Preparation of Luting Cements:

Using a double barrel syringe (MixPac, 1:1/V:V, static mixer:ML 2.5-12-S), acidic- and neutral pastes are mixed according to table 4.

Results:

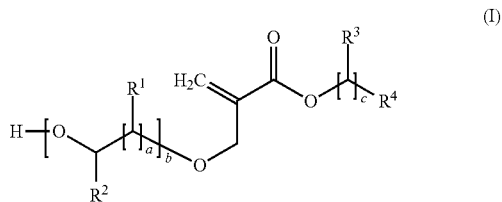

wherein
R$^1$ and R$^2$
  may be the same or different, independently represent a hydrogen atom or a C$_{1-6}$ alkyl group or a C$_{1-6}$ fluoroalkyl group,
R$^3$ which may the same or different when more than one R$^3$ is present, independently represent a hydrogen atom or a C$_{1-6}$ alkyl group or a C$_{1-6}$ fluoroalkyl group;
R$^4$ represents a hydrogen atom or a C$_{1-6}$ alkyl group or a C$_{1-6}$ fluoroalkyl group;
a is an integer of from 1 to 4;
b is 0 or an integer of from 1 to 9; and
c is 0 or an integer of from 1 to 9.

2. The resin modified dental luting cement composition according to claim 1, wherein the resin modified dental luting cement composition has a crown retention when cured as measured of at least 150 N using a mock-crown set-up, and which has a crown-removability of at most 5 attempts as measured with a crown-removal instrument.

TABLE 4

| Physical data of implant cements formulations | | | | | | | | | | | |
|---|---|---|---|---|---|---|---|---|---|---|---|
| | | | | Covalent network/ | Reactive fillers/ | CR [N] | | CRB [N°] | | | | |
| Entry | Acidic paste | Neutral paste | Filler fraction [wt.-%] | (covalent + ionic network) [%] | (reactive fillers + PAA) [%] | metal | zirconia | metal | zirconia | CS [MPa] | FS [MPa] | FM [MPa] |
| Ex-1 | A1 | N1 | 50.8 | 30.49 | 88.82 | 309 | 247 | 2.8 | >20 | 72 | 11.1 | 1508 |
| Ex-2 | A2 | N2 | 47.8 | 34.80 | 89.08 | 198 | 320 | 2.0 | >20 | 74 | 11.2 | 1680 |
| Ex-3 | A3 | N3 | 45.2 | 39.39 | 89.94 | 219 | 233 | 1.2 | 3.2 | 56 | 10.8 | 1055 |
| Ex-4 | A4 | N4 | 42.5 | 44.28 | 91.36 | 133 | 134 | 1.2 | 2.0 | 37 | 10.1 | 1036 |
| Ex-5 | A5 | N5 | 39.9 | 49.28 | 92.32 | 108 | 110 | 1.2 | 2.0 | 19 | 6.7 | 460 |
| CEx-1 | A3 | NC1 | 45.2 | 39.39 | 89.94 | 171 | n.d. | 3.7 | n.d. | 48 | 11.1 | 780 |
| CEx-2 | A3 | NC2 | 45.2 | 39.39 | 89.94 | 149 | n.d. | 3.1 | n.d. | 43 | 9.5 | 530 |
| CEx-3 | A3 | NC3 | 45.2 | 39.39 | 89.94 | 178 | n.d. | 3.6 | n.d. | 71 | 12.5 | 1537 |

The invention claimed is:

1. A resin modified dental luting cement composition comprising
   (a) a polymerizable resin component;
   (b) a polyacidic polymer component;
   (c) a filler component comprising
      (c1) a particulate zinc oxide containing filler adapted to be reactive with the polyacidic polymer component in a cement reaction, and
      (c2) an inert particulate filler which cannot react with the polyacidic polymer in a cement reaction;
   (d) a redox initiator system for initiating polymerization of the polymerizable resin component, the redox initiator system comprising an oxidizing agent and a reducing agent; and
   (e) water
wherein the polymerizable resin component comprises a compound of formula (I):

3. The resin modified dental luting cement composition according to claim 1, wherein the polyacidic polymer component consists essentially of a polyacrylic acid having an average molecular weight Mw of from 10 to 75 kDa.

4. The resin modified dental luting cement composition according to claim 1, wherein the particulate zinc oxide containing filler has a mean particle size in a range of from 0.01 to 10 μm.

5. The resin modified dental luting cement composition according to claim 1, wherein the inert particular filler comprises a radiopaque filler and a nanofiller.

6. The resin modified dental luting cement composition according to claim 1, further comprising a photoinitiator and/or an antibacterial agent.

7. The resin modified dental luting cement composition according to claim 1, wherein the resin modified dental luting cement composition comprises based on the total weight of the composition
   (a) 10 to 30 percent by weight of the polymerizable resin component;

(b) 5 to 20 percent by weight of the polyacidic polymer component;

(c) 35 to 65 percent by weight of the filler component;

(d) 0.5 to 5 percent by weight of the redox initiator system; and (e) 10 to 30 percent by weight of water.

8. The resin modified dental luting cement composition according to claim 1, wherein the resin modified dental luting cement composition is a paste/paste composition consisting of a non-aqueous neutral paste and an aqueous acidic paste.

9. The resin modified dental luting cement composition according to claim 8, wherein the neutral paste contains the polymerizable resin component, the particulate zinc oxide containing filler adapted to be reactive with the polyacidic polymer component in a cement reaction, the oxidizing agent or reducing agent, and optionally an inert particulate filler, and wherein the acidic paste contains the polyacidic polymer component, the reducing agent or oxidizing agent, water and optionally the inert particulate filler.

10. The resin modified dental luting cement composition according to claim 1, wherein the oxidizing agent is a peroxide or hydroperoxide, and/or wherein the reducing agent is a thiourea compound.

11. The resin modified dental luting cement composition according to claim 1, wherein the resin modified dental luting cement composition is packaged in a two-barrel syringe or in a single use two-chamber unit.

12. The resin modified dental luting cement composition according to claim 1, wherein the resin modified dental luting cement is capable of adhering an implant restoration to an abutment.

\* \* \* \* \*